(12) United States Patent
Kiyomori et al.

(10) Patent No.: US 7,112,710 B2
(45) Date of Patent: Sep. 26, 2006

(54) PREPARATION OF SILYL KETENE ACETAL AND DISILYL KETENE ACETAL

(75) Inventors: Ayumu Kiyomori, Niigata-ken (JP); Tohru Kubota, Niigata-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 80 days.

(21) Appl. No.: 11/186,845

(22) Filed: Jul. 22, 2005

(65) Prior Publication Data

US 2005/0256329 A1     Nov. 17, 2005

Related U.S. Application Data

(62) Division of application No. 10/829,193, filed on Apr. 22, 2004, now Pat. No. 6,960,679.

(30) Foreign Application Priority Data

Apr. 25, 2003    (JP) .............................. 2003-121366

(51) Int. Cl.
     *C07F 7/18*      (2006.01)
(52) U.S. Cl. ....................... 570/466; 570/443; 570/465
(58) Field of Classification Search ................ 570/466, 570/465, 443
See application file for complete search history.

(56) References Cited

U.S. PATENT DOCUMENTS

| | | | |
|---|---|---|---|
| 4,417,034 A | 11/1983 | Webster | |
| 4,482,729 A | 11/1984 | Ishikawa et al. | |
| 4,508,880 A | 4/1985 | Webster | |
| 4,746,750 A | 5/1988 | Revis | |
| 4,780,554 A | 10/1988 | Quirk et al. | |
| 4,783,543 A | 11/1988 | Schulz, Jr. et al. | |
| 4,824,981 A | 4/1989 | Schulz, Jr. et al. | |
| 5,208,358 A | 5/1993 | Dinh et al. | |
| 2004/0127668 A1 | 7/2004 | Rubinsztajn et al. | |

FOREIGN PATENT DOCUMENTS

| | | |
|---|---|---|
| EP | 0184692 A1 | 6/1986 |
| EP | 0298363 A2 | 1/1989 |
| EP | 0305855 A2 | 3/1989 |
| EP | 0317960 A2 | 5/1989 |
| JP | 219322 A2 | 10/1986 |
| JP | 62-87594 A | 4/1987 |
| JP | 02199322 A2 | 4/1987 |
| JP | 63-290887 A | 11/1988 |
| JP | 64-71886 A | 3/1989 |
| JP | 64-85982 A | 3/1989 |
| JP | 2-111780 A | 4/1990 |
| JP | 0579457 A1 | 1/1994 |
| JP | 9-221444 A | 8/1997 |
| JP | 2001-247514 A | 9/2001 |

OTHER PUBLICATIONS

*J. Gen. Chem. (USSR)*, vol. 29, (1959), pp. 2896-2899.
*Chem. Pharm. Bull.*, vol. 22, (1974), pp. 2767-2769.
English language Abstract of JP 07025808 (Jan. 27, 1995).
Zhao et al., *Organic Letters*, vol. 3, No. 18, (2001), pp. 2839-2842.
Petrov et al., *J. of Gen. Chem. of the USSR*, vol. 20, (1959), pp. 2896-2899.
Yoshii et al., *Chem. and Pharm. Bull.*, vol. 22, No. 11, (1974), pp. 2767-2769.
Ishihara et al., *SYNLETT*, (1994), pp. 963-964.
Christmann et al., *Tetrahedron Letters*, vol. 42, (2001), pp. 1269-1271.
Ishihara et al., *Bull. Chem. Soc. Jpn.*, vol. 68, (1995), pp. 1721-1730.

*Primary Examiner*—Elvis O. Price
(74) *Attorney, Agent, or Firm*—Birch, Stewart, Kolasch & Birch, LLP

(57) ABSTRACT

By reacting α,β-unsaturated carboxylic esters with hydrosilanes or hydrosiloxanes in the presence of a catalytic amount of tris(pentafluorophenyl)borane, silyl ketene acetals or disilyl ketene acetals with high purity are produced in high yields.

1 Claim, No Drawings

PREPARATION OF SILYL KETENE ACETAL AND DISILYL KETENE ACETAL

CROSS REFERENCE TO RELATED APPLICATIONS

This application is a Divisional of application Ser. No. 10/829,193 filed on Apr. 22, 2004, now U.S. Pat. No. 6,960,679, and for which priority is claimed under 35 U.S.C. § 120; and this application claims priority of Application No. 2003-121366 filed in Japan on Apr. 25, 2003 under 35 U.S.C. § 119. The entire contents of both of these applications are hereby incorporated by reference.

FIELD OF THE INVENTION

This invention relates to processes for preparing silyl ketene acetals and disilyl ketene acetals which are useful as initiators for group transfer polymerization and intermediates for the synthesis of pharmaceutical, agricultural and various other organic compounds.

BACKGROUND ART

For silyl ketene acetals, Petrov et al. first reported their synthesis (see J. Gen. Chem. (USSR), 1959, vol. 29, pp. 2896–2899). The silyl ketene acetals are compounds of great commercial interest. One of their applications is the use as polymerization initiators in the polymerization of acrylate monomers, known as "group transfer polymerization," developed by Webster et al. (see U.S. Pat. No. 4,417,034 and U.S. Pat. No. 4,508,880). Another application is the use as nucleophilic agents in the synthesis of carboxylic acid derivatives (see JP-A 2001-247514).

Disilyl ketene acetals are regarded as one class of silyl ketene acetals from the standpoint of chemical structure. Therefore, most of their preparation processes are in accord with processes of silyl ketene acetal preparation.

Heretofore, for the preparation of silyl ketene acetals, four predominant processes are known in the art. They are (1) the reaction of a carboxylic ester having a hydrogen atom at α-position with a base and a silylating agent; (2) the activation of a carboxylic ester having a halogen atom substituted at α-position with a metal such as sodium or zinc, followed by reaction with a silylating agent such as chlorotrimethylsilane; (3) the reaction of a malonic ester with a silylating agent such as chlorotrimethylsilane in the presence of metallic sodium; and (4) the reaction of an α,β-unsaturated carboxylic ester with a hydrosilane or hydrosiloxane in the presence of a transition metal catalyst.

In process (1), typical combinations of base/silylating agent include lithium diisopropylamide/chlorotrimethylsilane (see JP-A9-221444, for example) and triethylamine/trimethylsilyl trifluoromethanesulfonate (see U.S. Pat. No. 4,482,729, for example). In either case, reaction proceeds at room temperature or lower temperatures, but requires to use at least one equivalent of the base, forming a large amount of salt. This is detrimental particularly when the process is applied to a large scale of production. The latter combination sometimes results in low yields with certain substrates because a compound having alpha-carbon silylated is produced in addition to the desired silyl ketene acetal.

In process (2) as exemplified by JP-A 2-111780 and process (3) as exemplified by JP-A 64-85982, at least one equivalent of a metal such as sodium is used, forming a large amount of metal salt. The metal salt must be removed before the desired silyl ketene acetal can be isolated. Also, since the metal is often used in excess, the metal salt formed contains metal in the activated state, requiring careful handling. Thus these processes are difficult to implement on a large scale.

Unlike processes (1) to (3), process (4) utilizes addition reaction, offering the advantage that no waste products like the above-mentioned salt are formed. It is known that this process uses transition metal compounds as the catalyst. In the article of Petrov et al., for example, a platinum compound is used as the catalyst. Among others, rhodium catalysts are effective. For instance, chlorotris(triphenylphosphine)rhodium is used in Chem. Pharm. Bull., 1974, vol. 22, pp. 2767–2769 and JP-A 63-290887 and rhodium trichloride trihydrate used in JP-A 62-87594. In U.S. Pat. No. 5,208,358 a successful use of chlorobis(di-tert-butylsulfide)rhodium as a catalyst has been disclosed in producing silyl ketene acetals with lower catalyst loadings. However, as described in JP-A 62-87594, when hydrosilylation reaction is catalyzed by transition metal catalysts, there are formed not only the desired silyl ketene acetal, but also by-products such as carbonyl adducts or β-adducts which have a boiling point close to the desired product and are difficult to separate by distillation. It is then difficult to obtain silyl ketene acetals with high purity. In JP-A 62-87594, a silyl ketene acetal is obtained in a highly pure form ($\geqq 95\%$) by using rhodium trichloride trihydrate as the catalyst and an excess amount of hydrosilane and converting the carbonyl adduct to a high-boiling compound. However, by this process, it was difficult to obtain silyl ketene acetals in high yields because of the decreased yields based on the hydrosilane used, and of the increased distillation residue leading to lower isolated yields.

Thus, the process of making silyl ketene acetals by hydrosilylation of α,β-unsaturated carboxylic esters is advantageous in that it does not essentially generate by-products such as salts. Nonetheless, with conventional transition metal catalysts, it suffers from the low selectivity owing to the formation of multiple products derived from a variety of hydrosilylation modes. It would be desirable to have a process of preparing a silyl ketene acetal at a good selectivity, high purity and high yield.

For the preparation of disilyl ketene acetals, any of the foregoing processes is applicable. The preparation of disilyl ketene acetals generally starts with silyl carboxylic esters, most of which are not commercially available. This necessitates the extra step of preparing silyl carboxylates beforehand through silylation of carboxylic acids, adding to the cost of manufacture.

A process other than stated above has been proposed for disilyl ketene acetal manufacturing: a reaction between α,β-unsaturated carboxylic esters and hydrosilanes in the presence of a rhodium catalyst (see JP-A 64-71886). With this process, disilyl ketene acetals can be obtained in one step using allyl esters of α,β-unsaturated carboxylic acids such as commercially available allyl methacrylate. Although the reaction mixture resulting from this process is allegedly free of a typical by-product, carbonyl adduct, the yield and purity of the desired product are below satisfactory levels because other by-products are formed in noticeable amounts.

The existing processes for the preparation of disilyl ketene acetals suffer from drawbacks such as large amounts of by-product generation and laborious purification of the desired compounds. It would be desirable to have a process of preparing disilyl ketene acetals in high purity and high yields without forming substantial by-products.

SUMMARY OF THE INVENTION

An object of the invention is to provide processes of preparing silyl ketene acetals and disilyl ketene acetals in high purity and high yields without forming substantial by-products such as salts.

The inventors have found that by reacting an α,β-unsaturated carboxylic ester with a hydrosilane or hydrosiloxane in the presence of a catalytic amount of tris(pentafluorophenyl)borane, a silyl ketene acetal or disilyl ketene acetal with high purity is produced in high yields depending on the ratio of the α,β-unsaturated carboxylic ester and the hydrosilane or hydrosiloxane.

A first embodiment of the invention is a process for preparing a silyl ketene acetal of the general formula (3), comprising the step of reacting an α,β-unsaturated carboxylic ester of the general formula (1) with a hydrosilane or hydrosiloxane of the general formula (2) in the presence of a catalytic amount of tris(pentafluorophenyl)borane.

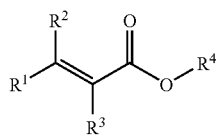
(1)

Herein $R^1$, $R^2$ and $R^3$ are each independently hydrogen or a substituted or unsubstituted monovalent hydrocarbon group of 1 to 60 carbon atoms, or a pair of $R^1$ and $R^2$ or $R^1$ and $R^3$ may bond together to form a ring of 3 to 20 carbon atoms with the carbon atom(s) to which they are attached, and $R^4$ is a substituted or unsubstituted monovalent hydrocarbon group of 1 to 40 carbon atoms or a substituted or unsubstituted silyl group of up to 60 carbon atoms and free of a SiH bond.

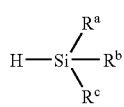
(2)

Herein $R^a$, $R^b$ and $R^c$ are independently selected from a substituted or unsubstituted monovalent hydrocarbon group of 1 to 20 carbon atoms, an organoxy group of 1 to 20 carbon atoms, an organo(poly)siloxy group of 1 to 1,000 silicon atoms, and a halogen atom, or a pair of $R^a$ and $R^b$, $R^a$ and $R^c$, or $R^b$ and $R^c$ may bond together to form a siloxane ring of 3 to 50 silicon atoms or a silicon-containing ring of 1 to 20 carbon atoms with the silicon atom to which they are attached, or $R^a$, $R^b$ and $R^c$ may bond together to form a cage siloxane of 6 to 50 silicon atoms with the silicon atom to which they are attached.

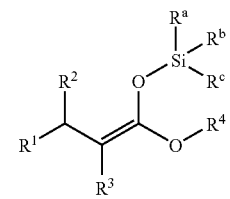
(3)

Herein $R^1$, $R^2$, $R^3$, $R^4$, $R^a$, $R^b$ and $R^c$ are as defined in formulae (1) and (2).

In one preferred embodiment, a reactor is charged with a mixture of the hydrosilane or hydrosiloxane of formula (2) and a catalytic amount of tris(pentafluorophenyl)borane, and the α,β-unsaturated carboxylic ester of formula (1) is then added to the reactor.

In another preferred embodiment, a reactor is charged with a catalytic amount of tris(pentafluorophenyl)borane, and the α,β-unsaturated carboxylic ester of formula (1) and the hydrosilane or hydrosiloxane of formula (2) are then added to the reactor in controlled amounts so as to provide 0.9 to 1.1 moles of Si—H bonds on the compound of formula (2) per mole of the compound of formula (1).

A second embodiment of the invention is a process for preparing a disilyl ketene acetal of the general formula (5), comprising the step of reacting an α,β-unsaturated carboxylic ester of the general formula (4) with a hydrosilane or hydrosiloxane of the general formula (2) in the presence of a catalytic amount of tris(pentafluorophenyl)borane.

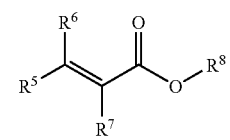
(4)

Herein $R^5$, $R^6$ and $R^7$ are each independently hydrogen or a substituted or unsubstituted monovalent hydrocarbon group of 1 to 60 carbon atoms, or a pair of $R^5$ and $R^6$ or $R^5$ and $R^7$ may bond together to form a ring of 3 to 20 carbon atoms with the carbon atom(s) to which they are attached, and $R^8$ is a substituted or unsubstituted monovalent hydrocarbon group of 1 to 40 carbon atoms.

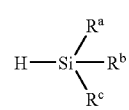
(2)

Herein $R^a$, $R^b$ and $R^c$ are as defined above.

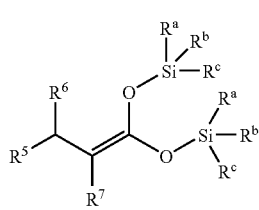

(5)

Herein $R^5$, $R^6$, $R^7$, $R^a$, $R^b$ and $R^c$ are as defined in formulae (4) and (2).

In a preferred embodiment, a reactor is charged with a mixture of the hydrosilane or hydrosiloxane of formula (2) and a catalytic amount of tris(pentafluorophenyl)borane, and the α,β-unsaturated carboxylic ester of formula (4) is then added to the reactor in an amount of up to 0.5 mole per mole of Si—H bonds on the compound of formula (2).

A third embodiment of the invention is a process for preparing a disilyl ketene acetal of the general formula (7), comprising the step of reacting a silyl ketene acetal of the general formula (6) with a hydrosilane or hydrosiloxane of the general formula (2) in the presence of a catalytic amount of tris(pentafluorophenyl)borane.

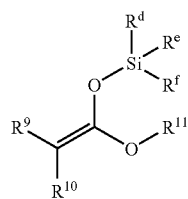

(6)

Herein $R^9$ and $R^{10}$ are each independently hydrogen or a substituted or unsubstituted monovalent hydrocarbon group of 1 to 60 carbon atoms, or a pair of $R^9$ and $R^{10}$ may bond together to form a ring of 3 to 20 carbon atoms with the carbon atom to which they are attached, $R^{11}$ is a substituted or unsubstituted monovalent hydrocarbon group of 1 to 40 carbon atoms, $R^d$, $R^e$ and $R^f$ are independently selected from a substituted or unsubstituted monovalent hydrocarbon group of 1 to 20 carbon atoms, an organoxy group of 1 to 20 carbon atoms, an organo(poly)siloxy group of 1 to 1,000 silicon atoms, and a halogen atom, or a pair of $R^d$ and $R^e$, $R^d$ and $R^f$ or $R^e$ and $R^f$ may bond together to form a siloxane ring of 3 to 50 silicon atoms or a silicon-containing ring of 1 to 20 carbon atoms with the silicon atom to which they are attached, or $R^d$, $R^e$ and $R^f$ may bond together to form a cage siloxane of 6 to 50 silicon atoms with the silicon atom to which they are attached.

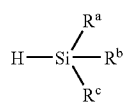

(2)

Herein $R^a$, $R^b$ and $R^c$ are as defined above.

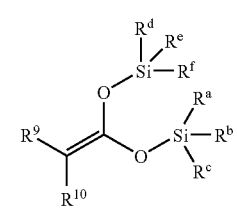

(7)

Herein $R^9$, $R^{10}$, $R^a$, $R^b$, $R^c$, $R^d$, $R^e$ and $R^f$ are as defined in formulae (6) and (2).

With the processes of the present invention, silyl ketene acetals and disilyl ketene acetals with high purity can be produced in high yields without forming substantial by-products such as salts. The silyl ketene acetals obtained by the process of the first embodiment are quite useful in polymer synthesis and organic synthesis. Using raw materials which are available on a commercial scale, the process of the second embodiment is able to produce in one stage disilyl ketene acetals which are commercially quite useful in polymer synthesis and organic synthesis.

DESCRIPTION OF THE PREFERRED EMBODIMENTS

In the first embodiment of the invention, silyl ketene acetals are prepared using α,β-unsaturated carboxylic acid esters of the general formula (1) as the starting material.

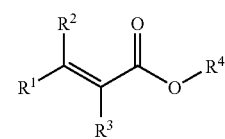

(1)

In formula (1), each of $R^1$, $R^2$ and $R^3$ is independently hydrogen or a substituted or unsubstituted monovalent hydrocarbon group of 1 to 60 carbon atoms, preferably 1 to 20 carbon atoms. Preferred unsubstituted monovalent hydrocarbon groups are those of 1 to 20 carbon atoms. The substituted monovalent hydrocarbon groups correspond to the unsubstituted monovalent hydrocarbon groups in which some or all of the hydrogen atoms bonded to carbon atoms are substituted with substituent groups. Suitable substituent groups include halogen atoms, alkoxy groups of 1 to 20 carbon atoms, preferably 1 to 10 carbon atoms, organoxy groups such as alkenyloxy and aryloxy groups, silyl groups of up to 60 carbon atoms and free of a SiH bond, and organo(poly)siloxy groups of 1 to 1,000 silicon atoms, preferably 1 to 50 silicon atoms, most preferably 1 to 10 silicon atoms.

Examples of the groups represented by $R^1$, $R^2$ and $R^3$ include straight, branched or cyclic, substituted or unsubstituted alkyl groups such as methyl, chloromethyl, bromobutyl, iodomethyl, trifluoromethyl, trimethylsilylmethyl, tris(trimethylsiloxy)silylmethyl, tris(trimethylsiloxy)siloxymethyl, ethyl, 2-methoxyethyl, 2-ethoxyethyl, 2-trimethylsiloxyethyl, 2-triethylsiloxyethyl, n-propyl, 3-(trimethoxysilyl)propyl, 3-(triethoxysilyl)propyl, 3-tris(trimethylsiloxy)silylpropyl, 3-(3,5,7,9,11,13,15-heptacyclopentylpentacyclo-[9.5.1.1$^{3,9}$.1$^{5,15}$.1$^{7,13}$] octasiloxan-1-yl)propyl, (3,5,7,9,11,13,15- heptacyclopentylpentacyclo-[9.5.1.1$^{3,9}$.1$^{5,15}$.1$^{7,13}$] octasiloxan-1-yloxydimethylsilyl)methyl, 3-(3,5,7,9,11,13,15-heptaisobutylpentacyclo-[9.5.1.1$^{3,9}$.1$^{5,15}$.1$^{7,13}$] octasiloxan-1-yl)propyl, 3-(pentamethyldisiloxanyloxy) propyl, 3-(ω-butylpolydimethylsiloxan-1-yloxy)propyl, isopropyl, n-butyl, isobutyl, tert-butyl, pentyl, cyclopentyl, hexyl, cyclohexyl, octyl, decyl, dodecyl, and stearyl; straight, branched or cyclic, substituted or unsubstituted alkenyl groups such as vinyl, propenyl, isopropenyl, butenyl, hexenyl, cyclohexenyl, decenyl and undecenyl; straight, branched or cyclic, substituted or unsubstituted alkynyl groups such as ethynyl, propynyl and butynyl; substituted or unsubstituted aryl groups such as phenyl, 4-fluorophenyl, 4-tert-butylphenyl, pentafluorophenyl, 2-tolyl, 3-tolyl, 4-tolyl, 2,6-dimethylphenyl, 2,4-dimethylphenyl, 3,5-dimethylphenyl, 3,4-dimethylphenyl, 2,5-dimethylphenyl, naphthyl and biphenylyl; and substituted or unsubstituted aralkyl groups such as benzyl, 2-chlorobenzyl, 4-bromobenzyl, 4-methoxybenzyl, phenylethyl and phenylpropyl.

In formula (1), a pair of $R^1$ and $R^2$ or a pair of $R^1$ and $R^3$ may bond together to form a ring of 3 to 20 carbon atoms, especially 5 to 12 carbon atoms, with the carbon atom or atoms to which they are attached. Suitable rings include cyclopentene, cyclohexene, cycloheptene, cyclooctene, cyclooctadiene, norbornene and indene rings.

In formula (1), $R^4$ is a substituted or unsubstituted monovalent hydrocarbon group of 1 to 40 carbon atoms, preferably 1 to 20 carbon atoms, or a substituted or unsubstituted silyl group of up to 60 carbon atoms and free of a SiH bond. Preferred unsubstituted monovalent hydrocarbon groups are those of 1 to 20 carbon atoms. Preferred unsubstituted, SiH bond-free silyl groups are those of up to 40 carbon atoms. The substituted monovalent hydrocarbon and substituted organosilyl groups correspond to the unsubstituted monovalent hydrocarbon and unsubstituted organosilyl groups, respectively, in which some or all of the hydrogen atoms bonded to carbon atoms are substituted with substituent groups. Suitable substituent groups include halogen atoms, alkoxy groups of 1 to 20 carbon atoms, preferably 1 to 10 carbon atoms, organoxy groups such as alkenyloxy and aryloxy groups, silyl groups of up to 60 carbon atoms and free of a SiH bond, and organo(poly)siloxy groups of 1 to 1,000 silicon atoms, preferably 1 to 200 silicon atoms. Examples of $R^4$ include the groups exemplified above for $R^1$, $R^2$ and $R^3$ as well as organosilyl groups such as trimethylsilyl, chloromethyldimethylsilyl, (trimethylsilylmethyl)dimethylsilyl, ethyldimethylsilyl, 3-chloropropyldimethylsilyl, 3,3,3-trifluoropropyldimethylsilyl, diethylmethylsilyl, triethylsilyl, tripropylsilyl, triisopropylsilyl, tributylsilyl, triisobutylsilyl, tert-butyldimethylsilyl, cyclopentyldimethylsilyl, hexyldimethylsilyl, cyclohexyldimethylsilyl, thexyldimethylsilyl, thexyldiisopropylsilyl, decyldimethylsilyl, octadecyldimethylsilyl, benzyldimethylsilyl, dimethylphenylsilyl, methyldiphenylsilyl, triphenylsilyl, tri-p-tolylsilyl, tri-o-tolylsilyl, methoxydimethylsilyl, dimethoxymethylsilyl, trimethoxysilyl, ethyldimethoxysilyl, propyldimethoxysilyl, ethoxydimethylsilyl, diethoxymethylsilyl, triethoxysilyl, isopropoxydimethylsilyl, sec-butoxydimethylsilyl, tert-butoxydimethylsilyl, dimethylphenoxysilyl, benzyloxydimethylsilyl, chlorodimethylsilyl, dichloromethylsilyl, trichlorosilyl, chlorodiethylsilyl, dichloroethylsilyl, chlorodiphenylsilyl, dichlorophenylsilyl, pentamethyldisiloxanyl, 3-chloropropyl-1,1,3,3-tetramethyldisiloxanyl, 1,1,3,3,5,5,5-heptamethyltrisiloxanyl, 1,1,1,3,5,5,5-heptamethyltrisiloxanyl, 1,3,3,5,5,7,7-heptamethylcyclotetrasiloxan-1-yl, tris(trimethylsiloxy) silyl, 3,5,7,9,11,13,15-heptacyclopentylpentacyclo [9.5.1.1$^{3,9}$.1$^{5,15}$.1$^{7,13}$]octasiloxan-1-yl, 3,5,7,9,11,13,15-heptacyclopentylpenta-cyclo[9.5.1.1$^{3,9}$.1$^{5,15}$.1$^{7,13}$]octasiloxan-1-yloxydimethylsilyl, and ω-butylpolydimethylsiloxan-1-yl.

Illustrative, non-limiting, examples of the α,β-unsaturated carboxylic esters of formula (1) include methyl acrylate, ethyl acrylate, 2-methoxyethyl acrylate, 2-ethoxyethyl acrylate, butyl acrylate, tert-butyl acrylate, cyclohexyl acrylate, 1,1,2-trimethylpropyl acrylate, vinyl acrylate, allyl acrylate, isopropenyl acrylate, 1-cyclohexenyl acrylate, 10-undecenyl acrylate, ethynyl acrylate, trimethylsilyl acrylate, triethylsilyl acrylate, triisopropylsilyl acrylate, tert-butyldimethylsilyl acrylate, methyl methacrylate, ethyl methacrylate, 2-methoxyethyl methacrylate, 2-ethoxyethyl methacrylate, 2-trimethylsiloxyethyl methacrylate, 2-chloropropyl methacrylate, 3-triethylsilylpropyl methacrylate, 3-(trimethoxysilyl)propyl methacrylate, 3-(triethoxysilyl) propyl methacrylate, 3-tris(trimethylsiloxy)silylpropyl methacrylate, 3-(3,5,7,9,11,13,15-heptacyclopentylpentacyclo-[9.5.1.1$^{3,9}$.1$^{5,15}$.1$^{7,13}$]octasiloxan-1-yl)propyl methacrylate, 3-(3,5,7,9,11,13,15-heptaisobutylpentacyclo-[9.5.1.1$^{3,9}$.1$^{5,15}$.1$^{7,13}$]octasiloxan-1-yl)propyl methacrylate, (3,5,7,9,11,13,15-heptacyclopentylpentacyclo-[9.5.1.1$^{3,9}$.1$^{5,15}$.1$^{7,13}$]octasiloxan-1-yloxydimethylsilyl)methyl methacrylate, 3-(3,5,7,9,11,13,15-heptacyclopentylpentacyclo-[9.5.1.1$^{3,9}$.1$^{5,15}$.1$^{7,13}$]octasiloxan-1-yloxydimethylsilyl)propyl methacrylate, butyl methacrylate, isobutyl methacrylate, tert-butyl methacrylate, cyclohexyl methacrylate, 1,1,2-trimethylpropyl methacrylate, 2-ethylhexyl methacrylate, decyl methacrylate, isobornyl methacrylate, octadecyl methacrylate, vinyl methacrylate, allyl methacrylate, isopropenyl methacrylate, 1-cyclohexenyl methacrylate, 10-undecenyl methacrylate, ethynyl methacrylate, benzyl methacrylate, phenyl methacrylate, trimethylsilyl methacrylate, (3-chloropropyldimethylsilyl)methacrylate, (dimethyl-3,3,3-trifluoropropylsilyl)methacrylate, triethylsilyl methacrylate, triisopropylsilyl methacrylate, tert-butyldimethylsilyl methacrylate, (1,1,3,3,3-pentamethyldisiloxan-1-yl)methacrylate, (1,3,3,5,5,7,7-heptamethylcyclotetrasiloxan-1-yl) methacrylate, (3,5,7,9,11,13,15-heptacyclopentylpentacyclo-[9.5.1.1$^{3,9}$.1$^{5,15}$.1$^{7,13}$]octasiloxan-1-yl)methacrylate, (3,5,7,9,11,13,15-heptaisobutylpentacyclo-[9.5.1.1$^{3,9}$.1$^{5,15}$.1$^{7,13}$]octasiloxan-1-yl)methacrylate, (3,5,7,9,11,13,15-heptacyclopentylpentacyclo-[9.5.1.1$^{3,9}$.1$^{5,15}$.1$^{7,13}$] octasiloxan-1-yloxydimethylsilyl)methacrylate, methyl crotonate, methyl cinnamate, ethyl 4-chlorocinnamate, methyl 4-methoxycinnamate, methyl 1-cyclohexenecarboxylate, methyl cyclohexylidene-acetate, 1,1,3,3,3-pentamethyl-1-[3-(methacryloyloxy)propyl]-disiloxane, and α-[3-(methacryloyloxy)propyl]-ω-butyl-polydimethylsiloxane.

In the process for preparing a silyl ketene acetal according to the first embodiment of the invention, the α,β-unsaturated carboxylic ester of formula (1) is reacted with a hydrosilane or hydrosiloxane of the following general formula (2).

(2)

In formula (2), each of $R^a$, $R^b$ and $R^c$ is independently selected from among a substituted or unsubstituted monovalent hydrocarbon group of 1 to 20 carbon atoms, preferably 1 to 10 carbon atoms, an organoxy group of 1 to 20 carbon atoms, preferably 1 to 10 carbon atoms, an organo(poly)siloxy group of 1 to 1,000 silicon atoms, and a halogen atom.

Examples of the groups represented by $R^a$, $R^b$ and $R^c$ include straight, branched or cyclic, substituted or unsubstituted alkyl groups such as methyl, chloromethyl, trifluoromethyl, ethyl, propyl, 3-chloropropyl, 3,3,3-trifluoropropyl, isopropyl, butyl, isobutyl, sec-butyl, tert-butyl, pentyl, cyclopentyl, hexyl, cyclohexyl, octyl, decyl, dodecyl, and stearyl; substituted or unsubstituted aryl groups such as phenyl, 4-fluorophenyl, 4-chlorophenyl, 4-bromophenyl, 4-iodophenyl, pentafluorophenyl, tolyl, xylyl, naphthyl and biphenylyl; substituted or unsubstituted aralkyl groups such as benzyl, phenylethyl and phenylpropyl; substituted or unsubstituted alkoxy groups such as methoxy, ethoxy, propoxy, isopropoxy, butoxy, sec-butoxy, tert-butoxy, isobutoxy, cyclopentyloxy, cyclohexyloxy, and norbornyloxy; substituted or unsubstituted aryloxy groups such as phenoxy, 3-chlorophenoxy and naphthyloxy; substituted or unsubstituted aralkyloxy groups such as benzyloxy, 2-chlorobenzyloxy, 3-chlorobenzyloxy, 4-chlorobenzyloxy and naphthylethyloxy; and straight, branched or cyclic, substituted or unsubstituted organo(poly)siloxy groups such as dimethylsiloxy, diethylsiloxy, diphenylsiloxy, trimethylsiloxy, chloromethyldimethylsiloxy, triethylsiloxy, phenyldimethylsiloxy, diphenylmethylsiloxy, 1,1,3,3,3-pentamethyldisiloxanyloxy, 1,1,3,3-tetramethyldisiloxanyloxy, bis(trimethylsiloxy)siloxy, methylbis(trimethylsiloxy)siloxy, tris(trimethylsiloxy)siloxy, 1,3,3,5,5-pentamethylcyclotrisiloxan-1-yloxy, 1,3,5-trimethyl-3,5-bis(3,3,3-trifluoropropyl)cyclo-trisiloxan-1-yloxy, 1,3,5,7-tetramethylcyclotetrasiloxan-1-yloxy, ω-methylpolydimethylsiloxanyloxy, ω-hydropolydimethylsiloxanyloxy, and polyhydromethylsiloxanyloxy.

A pair of $R^a$ and $R^b$, a pair of $R^a$ and $R^c$, or a pair of $R^b$ and $R^c$ may bond together to form a siloxane ring of 3 to 50 silicon atoms, preferably 3 to 20 silicon atoms, or a silicon-containing ring of 1 to 20 carbon atoms with the silicon atom to which they are attached. Alternatively, $R^a$, $R^b$ and $R^c$ may bond together to form a cage siloxane of 6 to 50 silicon atoms, preferably 6 to 20 silicon atoms with the silicon atom to which they are attached. Illustrative, non-limiting examples of cage siloxane rings are given below.

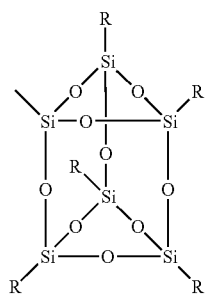
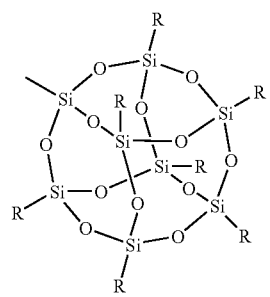
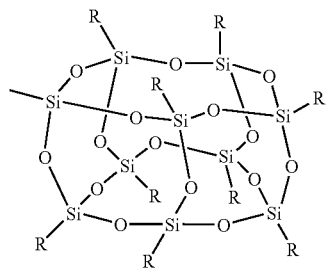

Illustrative, non-limiting examples of the compounds of formula (2) include organohydrosilanes such as trimethylsilane, chloromethyldimethylsilane, (trimethylsilylmethyl)dimethylsilane, ethyldimethylsilane, 3-chloropropyldimethylsilane, 3,3,3-trifluoropropyldimethylsilane, diethylmethylsilane, triethylsilane, tripropylsilane, triisopropylsilane, tributylsilane, triisobutylsilane, tert-butyldimethylsilane, cyclopentyldimethylsilane, hexyldimethylsilane, cyclohexyldimethylsilane, thexyldimethylsilane, thexyldiisopropylsilane, decyldimethylsilane, octadecyldimethylsilane, benzyldimethylsilane, dimethylphenylsilane, methyldiphenylsilane, triphenylsilane, tri-p-tolylsilane, tri-o-tolylsilane, 1,4-bis(dimethylsilyl)benzene, methoxydimethylsilane, dimethoxymethylsilane, trimethoxysilane, ethyldimethoxysilane, propyldimethoxysilane, ethoxydimethylsilane, diethoxymethylsilane, triethoxysilane, isopropoxydimethylsilane, sec-butoxydimethylsilane, tert-butoxydimethylsilane, dimethylphenoxysilane, benzyloxydimethylsilane, chlorodimethylsilane, dichloromethylsilane, trichlorosilane, chlorodiethylsilane, dichloroethylsilane, chlorodiphenylsilane, and dichlorophenylsilane; and straight, branched, cyclic or cage organohydrosiloxanes such as pentamethyldisiloxane, 3-chloropropyl-1,1,3,3-tetramethyldisiloxane, 1,1,3,3,5,5,5-heptamethyltrisiloxane, 1,1,3,3-tetramethyldisiloxane, 1,1,3,3-tetraisopropyldisiloxane, 1,3-dimethyl-1,3-diphenyldisiloxane, 1,1,3,3,5,5-hexamethyltrisiloxane, 1,1,1,3,5,5,5-heptamethyltrisiloxane, 1,1,1,3,5,7,7,7-octamethyltetrasiloxane, 1,3,5,7-tetramethylcyclotetrasiloxane, tris(trimethylsiloxy)silane, 1-hydrido-3,5,7,9,11,13,15-heptacyclopentylpentacyclo-[9.5.1.1$^{3,9}$.1$^{5,15}$.1$^{7,13}$]octasiloxane, 1-(hydridodimethylsiloxy)-3,5,7,9,11,13,15-heptacyclopentyl-pentacyclo[9.5.1.1$^{3,9}$.1$^{5,15}$.1$^{7,13}$]octasiloxane, 1,3,5,7,9,11,13,15-octakis(dimethylsiloxy)pentacyclo-[9.5.1.1$^{3,9}$.1$^{5,15}$.1$^{7,13}$]octasiloxane, α-hydro-ω-methylpolydimethylsiloxane, α,ω-dihydropolydimethylsiloxane, and polymethylhydrosiloxane.

Preferably the compound of formula (2) is used in such amounts as to provide 0.9 to 1.1 moles of Si—H bonds on the compound of formula (2) per mole of the compound of formula (1). If either one of the compounds of formulae (1) and (2) is used in large excess, the percent yield of the product based on that compound is reduced and side reactions may occur in a more proportion to further reduce the yield.

In the preparation of silyl ketene acetals according to the first embodiment of the invention, the compound of formula (1) is reacted with the compound of formula (2) in the presence of a catalytic amount of tris(pentafluorophenyl) borane. The amount of tris(pentafluorophenyl)borane used varies with the reaction substrates although it is usually 0.00001 to 10 mol %, preferably 0.0001 to 1 mol % based on the compound of formula (1).

The reaction is generally effected under atmospheric pressure and in an inert gas atmosphere such as nitrogen although the process is not limited thereto. The reaction temperature is usually in the range of −100° C. to 100° C., preferably −20° C. to 60° C. For the preparation of a silyl ketene acetal, the compound of formula (1) wherein $R^4$ is bonded to the oxygen atom via primary or secondary $sp^3$ carbon is often used in the following embodiments. In one embodiment wherein the α,β-unsaturated carboxylic ester of formula (1) is added to a reactor charged with a mixture of the hydrosilane or hydrosiloxane of formula (2) and a catalytic amount of tris(pentafluorophenyl)borane, the reaction temperature is preferably set in the range of −100° C. to −20° C. In another embodiment wherein a reactor is charged with a catalytic amount of tris(pentafluorophenyl)borane, and the α,β-unsaturated carboxylic ester of formula (1) and the hydrosilane or hydrosiloxane of formula (2) are added to the reactor in controlled amounts so as to provide 0.9 to 1.1 moles of Si—H bonds on the compound of formula (2) per mole of the compound of formula (1), the reaction temperature is preferably set in the range of −50° C. to 30° C.

Any desired mode may be used in the mixing of the substrates and the catalyst as long as attention is paid to the fact that the α,β-unsaturated carboxylic ester of formula (1) is generally polymerizable. To control reaction conditions to suppress the possibility of polymerization, it is recommended that the reaction be performed by feeding the compound of formula (1) to a reactor charged with the catalyst and the compound of formula (2) or by feeding both the compounds of formulae (1) and (2) to a reactor charged with the catalyst. In the latter case, the compounds are preferably fed in controlled rates so as to provide 0.9 to 1.1 moles of Si—H bonds on the compound of formula (2) per mole of the compound of formula (1).

A reaction solvent is not always necessary. Especially when both the reaction substrates (1) and (2) are liquid, the reaction can proceed in a solventless system. Of course, a solvent may be used for the reaction to take place. Suitable solvents include hydrocarbon solvents such as hexane, isooctane, benzene, toluene, and xylene, and halogenated hydrocarbon solvents such as dichloromethane and dichloroethane.

A polymerization inhibitor is optionally added during the reaction. Suitable polymerization inhibitors, if used, are hindered phenols such as 2,6-di-tert-butyl-4-methylphenol (BHT) and 1,3,5-tris(3,5-di-tert-butyl-4-hydroxybenzyl)-2,4,6-trimethylbenzene.

By the process in the first embodiment of the invention described above, the silyl ketene acetals of the following general formula (3) are obtainable.

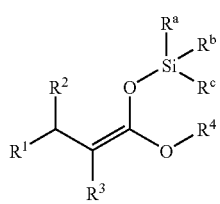

(3)

In formula (3), $R^1$, $R^2$, $R^3$, $R^4$, $R^a$, $R^b$ and $R^c$ are as defined above.

In the second embodiment of the invention, disilyl ketene acetals are prepared using α,β-unsaturated carboxylic acid esters of the general formula (4) as the starting material.

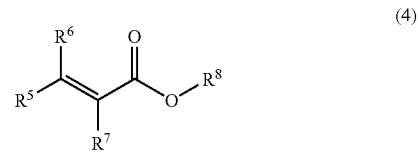

(4)

In formula (4), each of $R^5$, $R^6$ and $R^7$ is independently hydrogen or a substituted or unsubstituted monovalent hydrocarbon group of 1 to 60 carbon atoms, preferably 1 to 20 carbon atoms. Preferred unsubstituted monovalent hydrocarbon groups are those of 1 to 20 carbon atoms. The substituted monovalent hydrocarbon groups correspond to the unsubstituted monovalent hydrocarbon groups in which some or all of the hydrogen atoms bonded to carbon atoms are substituted with substituent groups. Suitable substituent groups include halogen atoms, alkoxy groups of 1 to 20 carbon atoms, preferably 1 to 10 carbon atoms, organoxy groups such as alkenyloxy and aryloxy groups, silyl groups of up to 60 carbon atoms and free of a SiH bond, and organo(poly)siloxy groups of 1 to 1,000 silicon atoms, preferably 1 to 50 silicon atoms, most preferably 1 to 10 silicon atoms. Examples of the groups represented by $R^5$, $R^6$ and $R^7$ are as exemplified for $R^1$, $R^2$ and $R^3$ in formula (1).

In formula (4), a pair of $R^5$ and $R^6$ or a pair of $R^5$ and $R^7$ may bond together to form a ring of 3 to 20 carbon atoms, especially 5 to 12 carbon atoms, with the carbon atom or atoms to which they are attached. Suitable rings include cyclopentene, cyclohexene, cycloheptene, cyclooctene, cyclooctadiene, norbornene and indene rings.

In formula (4), $R^8$ is a substituted or unsubstituted monovalent hydrocarbon group of 1 to 40 carbon atoms. Examples of the groups represented by $R^8$ are as exemplified for $R^1$, $R^2$ and $R^3$ in formula (1).

Illustrative, non-limiting, examples of the α,β-unsaturated carboxylic esters of formula (4) include methyl acrylate, ethyl acrylate, 2-methoxyethyl acrylate, 2-ethoxyethyl acrylate, butyl acrylate, tert-butyl acrylate, cyclohexyl acrylate, 1,1,2-trimethylpropyl acrylate, vinyl acrylate, allyl acrylate, isopropenyl acrylate, 1-cyclohexenyl acrylate, 10-undecenyl acrylate, ethynyl acrylate, methyl methacrylate, ethyl methacrylate, 2-methoxyethyl methacrylate, 2-ethoxyethyl methacrylate, 2-trimethylsiloxyethyl methacrylate, 2-chloropropyl methacrylate, 3-triethylsilylpropyl methacrylate, 3-(trimethoxysilyl)propyl methacrylate, 3-(triethoxysilyl)propyl methacrylate, 3-tris(trimethylsiloxy)silylpropyl methacrylate, 3-(3,5,7,9,11,13,15-heptacyclopentylpentacyclo-[9.5.1.1$^{3,9}$.1$^{5,15}$.1$^{7,13}$]octasiloxan-1-yl)propyl methacrylate, 3-(3,5,7,9,11,13,15-heptaisobutylpentacyclo-[9.5.1.1$^{3,9}$.1$^{5,15}$.1$^{7,13}$]octasiloxan-1-yl)propyl methacrylate, (3,5,7,9,11,13,15-heptacyclopentylpentacyclo-[9.5.1.1$^{3,9}$.1$^{5,15}$.1$^{7,13}$] octasiloxan-1-yloxydimethylsilyl)methyl methacrylate, 3-(3,5,7,9,11,13,15-heptacyclopentylpentacyclo-[9.5.1.1$^{3,9}$.1$^{5,15}$.1$^{7,13}$]octasiloxan-1-yloxydimethylsilyl)propyl methacrylate, butyl methacrylate, isobutyl methacrylate, tert-butyl methacrylate, cyclohexyl methacrylate, 1,1,2-trimethylpropyl methacrylate, 2-ethylhexyl methacrylate, decyl methacrylate, isobornyl methacrylate, octadecyl methacrylate, vinyl methacrylate, allyl methacrylate, isopropenyl methacrylate, 1-cyclohexenyl methacrylate, 10-undecenyl methacrylate, ethynyl methacrylate, benzyl methacrylate, phenyl methacrylate, methyl crotonate, methyl cinnamate, ethyl 4-chlorocinnamate, methyl 4-methoxycinnamate, methyl 1-cyclohexenecarboxylate, methyl cyclohexylideneacetate, 1,1,3,3,3-pentamethyl-1-[3-(methacryloyloxy)propyl]disiloxane, and α-[3-(methacryloyloxy)propyl]-ω-butyl-polydimethylsiloxane.

In the process for preparing a disilyl ketene acetal according to the second embodiment of the invention, the α,β-unsaturated carboxylic ester of formula (4) is reacted with a hydrosilane or hydrosiloxane of the following general formula (2).

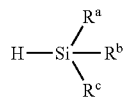

(2)

In formula (2), $R^a$, $R^b$ and $R^c$ are as defined above.

The compounds of formulae (4) and (2) are preferably used in such amounts that up to 0.5 mole of the compound of formula (4) is present per mole of Si—H bonds on the compound of formula (2). For efficient reaction, it is preferred to use 0.45 to 0.5 mole of the compound of formula (4) per mole of Si—H bonds.

In the preparation of disilyl ketene acetals according to the second embodiment of the invention, the compound of formula (4) is reacted with the compound of formula (2) in the presence of a catalytic amount of tris(pentafluorophenyl) borane. The amount of tris(pentafluorophenyl)borane used varies with the reaction substrates although it is usually 0.00001 to 10 mol %, preferably 0.001 to 1 mol % based on the compound of formula (4).

The reaction is generally effected under atmospheric pressure and in an inert gas atmosphere such as nitrogen although the process is not limited thereto. The reaction temperature is usually in the range of –100° C. to 100° C., preferably 0° C. to 60° C.

Any desired mode may be used in the mixing of the substrates and the catalyst as long as attention is paid to the fact that the α,β-unsaturated carboxylic ester of formula (4) is generally polymerizable like the compound of formula (1). To control reaction conditions to suppress the possibility of polymerization, it is recommended that the reaction be performed by feeding the compound of formula (4) to a reactor charged with the catalyst and the compound of formula (2).

A reaction solvent is not always necessary. Especially when both the reaction substrates (4) and (2) are liquid, the reaction can proceed in a solventless system. Of course, a solvent may be used for the reaction to take place. Suitable solvents include hydrocarbon solvents such as hexane, isooctane, benzene, toluene, and xylene, and halogenated hydrocarbon solvents such as dichloromethane and dichloroethane.

A polymerization inhibitor is optionally added during the reaction. Suitable polymerization inhibitors, if used, are hindered phenols such as 2,6-di-tert-butyl-4-methylphenol (BHT) and 1,3,5-tris(3,5-di-tert-butyl-4-hydroxybenzyl)-2,4,6-trimethylbenzene.

By the process in the second embodiment of the invention described above, the disilyl ketene acetals of the following general formula (5) are obtainable.

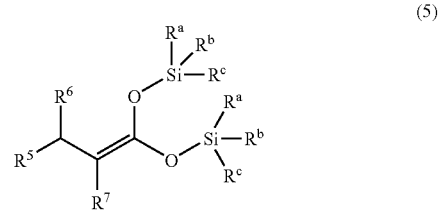

(5)

In formula (5), $R^5$, $R^6$, $R^7$, $R^a$, $R^b$ and $R^c$ are as defined above.

In the third embodiment of the invention, disilyl ketene acetals are prepared using silyl ketene acetals of the general formula (6) as the starting material.

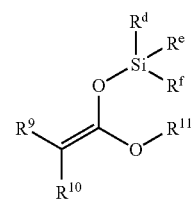

(6)

In formula (6), each of $R^9$ and $R^{10}$ is independently hydrogen or a substituted or unsubstituted monovalent hydrocarbon group of 1 to 60 carbon atoms, preferably 1 to 20 carbon atoms. Preferred unsubstituted monovalent hydrocarbon groups are those of 1 to 20 carbon atoms. The substituted monovalent hydrocarbon groups correspond to the unsubstituted monovalent hydrocarbon groups in which some or all of the hydrogen atoms bonded to carbon atoms are substituted with substituent groups. Suitable substituent groups include halogen atoms, alkoxy groups of 1 to 20 carbon atoms, preferably 1 to 10 carbon atoms, organoxy groups such as alkenyloxy and aryloxy groups, silyl groups of up to 60 carbon atoms and free of a SiH bond, and organo(poly)siloxy groups of 1 to 1,000 silicon atoms, preferably 1 to 50 silicon atoms, most preferably 1 to 10 silicon atoms.

Examples of the groups represented by $R^9$ and $R^{10}$ are as exemplified for $R^1$, $R^2$ and $R^3$ in formula (1).

In formula (6), a pair of $R^9$ and $R^{10}$ may bond together to form a ring of 3 to 20 carbon atoms, especially 5 to 12 carbon atoms, with the carbon atom to which they are attached. Suitable rings include cyclopentene, cyclohexene, cycloheptene, cyclooctene, cyclooctadiene, norbornene and indene rings.

In formula (6), $R^{11}$ is a substituted or unsubstituted monovalent hydrocarbon group of 1 to 40 carbon atoms. Examples of the groups represented by $R^{11}$ are as exemplified for $R^1$, $R^2$ and $R^3$ in formula (1).

Illustrative, non-limiting, examples of the compounds of formula (6) include 1-methoxy-1-trimethylsiloxyethene, 1-ethoxy-1-trimethylsiloxyethene, 1-butoxy-1-trimethylsiloxyethene, 1-methoxy-1-triethylsiloxyethene, 1-methoxy-1-trimethylsiloxypropene, 1-ethoxy-1-trimethylsiloxypropene, 1-butoxy-1-trimethylsiloxypropene, 1-(2-ethylhexyloxy)-1-trimethylsiloxypropene, 1-methoxy-1-triethylsiloxypropene, 1-methoxy-1-triisobutylsiloxypropene, 1-methoxy-1-(tert-butyldimethylsiloxy)propene, 1-methoxy-1- triisopropylsiloxypropene, 1-methoxy-2-methyl-1-trimethylsiloxypropene, 1-methoxy-2-methyl-1-triethylsiloxypropene, 1-methoxy-2-methyl-1-triisobutylsiloxypropene, 1-(tert-butyldimethylsiloxy)-1-methoxy-2-methylpropene, 1-methoxy-2-methyl-1-triisopropylsiloxypropene, 1-(chlorodimethylsiloxy)-1-methoxy-2-methylpropene, 1-(3-chloropropyldimethylsiloxy)-1-methoxy-2-methylpropene, 1-(ethoxydimethylsiloxy)-1-methoxy-2-methylpropene, 1-methoxy-2-methyl-1-phenyldimethylsiloxypropene, 1-methoxy-2-methyl-1-triphenylsiloxypropene, 1-methoxy-2-methyl-1-(tert-butyldiphenyl)siloxypropene, 1-methoxy-2-methyl-1-(pentamethyldisiloxanyloxy)propene, 1-ethoxy-2-methyl-1-triethylsiloxypropene, 1-isopropoxy-2-methyl-1-triethylsiloxypropene, 1-butoxy-2-methyl-1-triethylsiloxypropene, 1-tert-butoxy-2-methyl-1-triethylsiloxypropene, 2-methyl-1-triethylsiloxy-1-vinyloxypropene, 1-benzyloxy-2-methyl-1-triethylsiloxypropene, 1-cyclohexyloxy-2-methyl-1-triethylsiloxypropene, 1-(2-ethylhexyloxy)-2-methyl-1-triethylsiloxypropene, 1-(2-trimethylsiloxyethoxy)-2-methyl-1-trimethylsiloxypropene, 1-(2-triethylsiloxyethoxy)-2-methyl-1-triethylsiloxypropene, 1-methoxy-1-triethylsiloxybutene, and 1-methoxy-3-phenyl-1-triethylsiloxypropene.

In the process for preparing a disilyl ketene acetal according to the third embodiment of the invention, the silyl ketene acetal of formula (6) is reacted with a hydrosilane or hydrosiloxane of the formula (2).

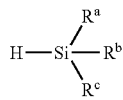

(2)

$R^a$, $R^b$ and $R^c$ are as defined above.

The compounds of formulae (6) and (2) may be used in any desired molar ratio. For efficient reaction, it is preferred to them in such amounts that 1.0 to 1.5 moles of Si—H bonds on the compound of formula (2) are available per mole of the compound of formula (6).

In the preparation of disilyl ketene acetals according to the third embodiment of the invention, the compound of formula (6) is reacted with the compound of formula (2) in the presence of a catalytic amount of tris(pentafluorophenyl) borane. The amount of tris(pentafluorophenyl)borane used varies with the reaction substrates although it is usually 0.00001 to 10 mol %, preferably 0.001 to 1 mol % based on the compound of formula (6).

The reaction is generally effected under atmospheric pressure and in an inert gas atmosphere such as nitrogen although the process is not limited thereto. The reaction temperature is usually in the range of −100° C. to 100° C., preferably 0° C. to 60° C.

Any desired mode may be used in the mixing of the substrates and the catalyst. In one exemplary mode, both the substrates are premixed in a reactor, to which the catalyst is added. In another exemplary mode, one substrate and the catalyst are premixed in a reactor, to which the other substrate is fed.

A reaction solvent is not always necessary. A solvent may be used for the reaction to take place. Suitable solvents that can be used herein include hydrocarbon solvents such as hexane, isooctane, benzene, toluene, and xylene, and halogenated hydrocarbon solvents such as dichloromethane and dichloroethane.

By the process in the third embodiment of the invention described above, the disilyl ketene acetals of the following general formula (7) are obtainable.

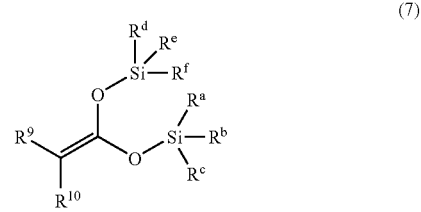

(7)

In formula (7), $R^9$, $R^{10}$, $R^a$, $R^b$, $R^c$, $R^d$, $R^e$ and $R^f$ are as defined above.

The silyl ketene acetals of formula (3) or the disilyl ketene acetals of formulae (5) and (7) obtained by the processes of the first to third embodiments can be isolated from the reaction mixture by distillation or the like. Since the amount of by-products such as carbonyl adducts is minimized, the silyl ketene acetal having high purity can be isolated simply by distillation. It is possible to deactivate the catalyst by adding a Lewis basic compound such as triethylamine or tributylamine to the reaction mixture prior to the isolation.

EXAMPLE

Examples of the invention are given below by way of illustration and not by way of limitation. In all examples, reaction was performed in a nitrogen atmosphere.

Example 1

Synthesis of 1-methoxy-2-methyl-1-triethylsiloxypropene through reaction of methyl methacrylate with triethylsilane A 100-mL four-necked flask equipped with a Dimroth reflux condenser, stirrer, thermometer and dropping funnel was purged with nitrogen. The flask was charged with 5.1 mg (0.01 mmol) of tris(pentafluorophenyl)borane (by Acros, lot No. A015140801, same hereinafter), 220 mg of BHT (Sumitomo Chemical Co., Ltd.) and 11.6 g (0.10 mol) of triethylsilane, which were stirred at room temperature for 0.5 hour. Using a dry ice/methanol bath, the flask was cooled to an internal temperature of −40 to −35° C. From the dropping funnel, 10.0 g (0.10 mol) of methyl methacrylate was added dropwise over 2 hours. Adjustment was made so as to maintain an internal temperature of −30 to −40° C. during the dropwise addition. Gas chromatography (GC) analysis confirmed the disappearance of methyl methacrylate after 5 minutes from the completion of dropwise addition. Neither a carbonyl adduct nor a β-adduct as shown below was detected. (Me is methyl, Et is ethyl.)

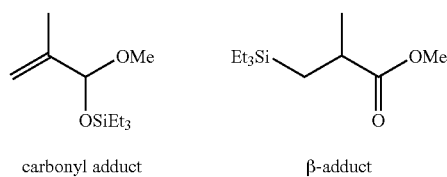

carbonyl adduct        β-adduct

After one hour from the completion of dropwise addition, the dry ice/methanol bath was removed and the flask was allowed to resume room temperature. Using a Claisen head having a Vigreux column having an inner diameter of 10 mm and a length of 10 cm, the faintly yellow, clear reaction solution was distilled in vacuo, whereby 17.4 g of a colorless clear liquid having a boiling point of 77–78° C./0.8 kPa was collected. From the results of NMR and GC/MS spectroscopy, the liquid was identified to be the title compound, 1-methoxy-2-methyl-1-triethylsiloxypropene. The yield was 80.4% and the purity was 98.8%.

$^1$H-NMR (CDCl$_3$, 300 MHz): δ (ppm) 3.51 (3H, s), 1.56 (3H, d, J=0.4 Hz), 1.53 (3H, d, J=0.4 Hz), 0.99 (9H, dt, J=0.7 Hz, 8.0 Hz), 0.69 (6H, dq, J=1.1 Hz, 7.9 Hz) $^{13}$C-NMR (CDCl$_3$, 75.6 MHz): δ (ppm) 149.8, 91.0, 57.1, 16.8, 16.1, 6.6, 4.9 $^{29}$Si-NMR (CDCl$_3$, 59.7 MHz): δ (ppm) 20.1 MS (EI): m/z 216 (M$^+$), 173, 117, 115, 89, 87, 86, 70, 59

Comparative Example 1

Synthesis of 1-methoxy-2-methyl-1-triethylsiloxypropene through reaction of methyl methacrylate with triethylsilane in the presence of rhodium trichloride trihydrate catalyst A 100-mL four-necked flask equipped with a Dimroth reflux condenser, stirrer, thermometer and dropping funnel was purged with nitrogen. The flask was charged with 2.6 mg (0.01 mmol) of rhodium trichloride trihydrate, 22 mg of BHT and 10.0 g (0.10 mol) of methyl methacrylate. With stirring, the flask was heated in an oil bath to an internal temperature of 51° C. From the dropping funnel, 11.6 g (0.10 mol) of triethylsilane was added dropwise over 3 hours. With dropwise addition, exothermic reaction took place. Adjustment was made so as to maintain an internal temperature of 54–60° C. After the completion of dropwise addition, the reaction mixture was stirred at 56–59° C. for one hour and at 65° C. for a further one hour, whereupon methyl methacrylate disappeared. GC and GC/MS analysis of the reaction mixture showed that the desired silyl ketene acetal was obtained as a main product, and the carbonyl adduct and β-adduct were additionally formed. The ratio silyl ketene acetal/carbonyl adduct/β-adduct of the products was 1:0.081:0.002 (TCD, GC area %). Using the same system as in Example 1, the reaction mixture was distilled in vacuo, whereby 18.1 g of a colorless clear fraction having a boiling point of 79–79.5° C./0.85 kPa was collected. On GC (TCD) analysis, the fraction had the following composition.

silyl ketene acetal: 94.5%
carbonyl adduct: 4.1%
β adduct: 0%
others: 1.4%

The result indicates the difficulty to isolate the title compound to high purity by distillation.

Example 2

Synthesis of 1,3-bis(1-methoxy-2-methyl-1-propenyloxy)-1,1,3,3-tetramethyldisiloxane through reaction of methyl methacrylate with 1,1,3,3-tetramethyldisiloxane A 100-mL four-necked flask equipped with a Dimroth reflux condenser, stirrer, thermometer and dropping funnel was purged with nitrogen. The flask was charged with 258 mg of 1,3,5-tris(3,5-di-tert-butyl-4-hydroxybenzyl)-2,4,6-trimethylbenzene (I-1330, Ciba Specialty Chemicals, same hereinafter), 5 mL of toluene and 0.5 mg (0.001 mmol) of tris(pentafluorophenyl)borane. With stirring, the flask was cooled to 2° C. in an ice water bath. From the dropping funnel, a mixture of 20.0 g (0.20 mol) of methyl methacrylate and 13.4 g (0.10 mol) of 1,1,3,3-tetramethyldisiloxane was added dropwise over 4 hours. During the period, the internal temperature rose to 7.5° C. at maximum. After the completion of dropwise addition, the reaction mixture was stirred at 2–4° C. for 1.5 hours whereupon methyl methacrylate disappeared. The reaction mixture was distilled in vacuo, whereby 26.5 g of a colorless clear fraction having a boiling point of 96–97.50° C./0.2 kPa was collected. From the results of NMR and GC/MS analysis, the liquid was identified to be the title compound, 1,3-bis(1-methoxy-2-methyl-1-propenyloxy)-1,1,3,3-tetramethyldisiloxane. The yield was 79.1%.

$^1$H-NMR (CDCl$_3$, 300 MHz): δ (ppm) 3.51 (6H, s), 1.56 (6H, d, J=0.4 Hz), 1.52 (6H, d, J=0.4 Hz), 0.20 (12H, s) $^{13}$C-NMR (CDCl$_3$, 75.6 MHz): δ (ppm) 148.7, 91.0, 56.6, 16.8, 16.1, −0.7 $^{29}$Si-NMR (CDCl$_3$, 59.7 MHz): δ (ppm) −12.2 MS (EI): m/z 334 (M$^+$), 233, 217, 179, 163, 133

Example 3

Synthesis of 2-methyl-1-triethylsiloxy-1-vinyloxypropene through reaction of vinyl methacrylate with triethylsilane A 100-mL four-necked flask equipped with a Dimroth reflux condenser, stirrer, thermometer and dropping funnel was purged with nitrogen. The flask was charged with 258 mg of I-1330, 7.7 mg (0.015 mmol) of tris(pentafluorophenyl)-borane and 11.6 g (0.10 mol) of triethylsilane, which were stirred at room temperature for 0.5 hour. The flask was cooled in an ice water bath to an internal temperature of 1.5° C. From the dropping funnel, 11.2 g (0.10 mol) of vinyl methacrylate was added dropwise over 2.5 hours. During the period, the internal temperature rose to 6.5° C. at maximum. After the completion of dropwise addition, the reaction mixture was stirred at 2° C. for 2 hours and with the ice water bath removed, at 15–20° C. for a further 5 hours. The reaction mixture was distilled in vacuo, whereby 19.3 g of a colorless clear fraction having a boiling point of 79.5–80° C./0.8 kPa was collected. From the results of NMR and GC/MS analysis, the liquid was identified to be the title compound, 2-methyl-1-triethylsiloxy-1-vinyloxypropene. The yield was 84.5%.

$^1$H-NMR (CDCl$_3$, 300 MHz): δ (ppm) 6.34 (1H, dd, J=6.3 Hz, 14.0 Hz), 4.49 (1H, dd, J=1.8 Hz, 14.0 Hz), 4.15 (1H, dd, J=1.8 Hz, 6.3 Hz), 1.58 (3H, d, J=0.4 Hz), 1.53 (3H, d, J=0.4 Hz), 0.98 (9H, dt, J=0.7 Hz, 7.9 Hz), 0.68 (6H, dq, J=1.2 Hz, 7.9 Hz) $^{13}$C-NMR (CDCl$_3$, 75.6 MHz): δ (ppm) 149.2, 146.3, 93.0, 90.7, 16.7, 16.1, 6.5, 5.0 $^{29}$Si-NMR (CDCl$_3$, 59.7 MHz): δ (ppm) 21.9 MS (EI): m/z 228 (M$^+$), 213, 115, 87, 70, 59

Example 4

Synthesis of 1-tert-butoxy-2-methyl-1-triethylsiloxypropene through reaction of tert-butyl methacrylate with triethylsilane A 100-mL four-necked flask equipped with a Dimroth reflux condenser, stirrer, thermometer and dropping funnel was purged with nitrogen. The flask was charged with 258 mg of I-1330, 7.7 mg (0.015 mmol) of tris(pentafluorophenyl)-borane and 11.6 g (0.10 mol) of triethylsilane, which were stirred at room temperature for 0.5 hour. The flask was cooled in an ice water bath to an internal temperature of 3.5° C. From the dropping funnel, 13.5 g (0.095 mol) of tert-butyl methacrylate was added dropwise over 2.5 hours. During the period, the internal temperature rose to 6° C. at maximum. After the completion of dropwise addition, the reaction mixture was stirred at 3–3.5° C. for 3 hours whereupon triethylsilane disappeared as confirmed by GC analysis. The reaction mixture contained a small amount of white solids. The reaction mixture was distilled in vacuo, whereby 24.8 g of a colorless clear fraction having a boiling point of 73–75° C./0.3 kPa was collected. From the results of NMR and MS analysis, the liquid was identified to be the title compound, 1-tert-butoxy-2-methyl-1-triethylsiloxypropene. The yield based on triethylsilane was 81.5%.

$^1$H-NMR (CDCl$_3$, 300 MHz): δ (ppm) 1.55 (3H, d, J=0.4 Hz), 1.54 (3H, d, J=0.4 Hz), 1.27 (9H, s), 0.98 (9H, dt, J=0.6 Hz, 7.8 Hz), 0.69 (6H, dq, J=1.1 Hz, 7.9 Hz) $^{13}$C-NMR (CDCl$_3$, 75.6 MHz): δ (ppm) 146.7, 95.6, 78.9, 29.1, 18.2, 17.5, 6.7, 5.2 $^{29}$Si-NMR (CDCl$_3$, 59.7 MHz): δ (ppm) 20.1MS (EI): m/z 258 (M$^+$), 229, 202, 173, 157, 133, 115, 103, 87, 75, 70, 57, 41

Example 5

Synthesis of 2-methyl-1-triethylsiloxy-1-trimethylsiloxy-propene through reaction of trimethylsilyl methacrylate with triethylsilane A 200-mL four-necked flask equipped with a Dimroth reflux condenser, stirrer, thermometer and dropping funnel was purged with nitrogen. The flask was charged with 258 mg of I-1330, 5.1 mg (0.01 mmol) of tris(pentafluorophenyl)-borane and 11.6 g (0.10 mol) of triethylsilane, which were stirred at room temperature for 15 minutes. The flask was cooled in an ice water bath to an internal temperature of 4.5° C. From the dropping funnel, 11.1 g (0.07 mol) of trimethylsilyl methacrylate was added dropwise over 4 hours. During the period, the internal temperature rose to 8° C. at maximum. A toluene solution of 3 mg (0.006 mmol) of tris(pentafluorophenyl)borane was added to the flask. From the dropping funnel, 4.7 g (0.03 mol) of trimethylsilyl methacrylate was then added dropwise over one hour. After the completion of dropwise addition, the reaction mixture was stirred at 5° C. for 9 hours whereupon triethylsilane disappeared as confirmed by GC analysis. The reaction mixture, to which 22 μL (0.16 mmol) of triethylamine was added, was stirred for 0.5 hour. Cooling was then stopped and the mixture allowed to warm to room temperature. The reaction mixture containing a small amount of white solids was distilled in vacuo, whereby 13.5 g of a colorless clear fraction having a boiling point of 69–71° C./0.4 kPa was collected. From the results of NMR and MS analysis, the liquid was identified to be the title compound, 2-methyl-1-triethylsiloxy-1-trimethylsiloxypropene. The yield was 49.2%.

$^1$H-NMR (CDCl$_3$, 300 MHz): δ (ppm) 1.53 (3H, s), 1.49 (3H, s) 0.98 (9H, t, J=7.9 Hz), 0.68 (6H, q, J=7.9 Hz), 0.18 (9H, s) $^{13}$C-NMR (CDCl$_3$, 75.6 MHz): δ (ppm) 145.0, 87.7, 17.4, 17.2, 6.7, 5.1, 0.4 $^{29}$Si-NMR (CDCl$_3$, 59.7 MHz): δ (ppm) 20.6, 19.6MS (EI): m/z 274 (M$^+$), 259, 231, 175, 147, 119, 115, 87, 86, 73, 59

Example 6

Synthesis of 1,1-bis(triethylsiloxy)-2-methylpropene through reaction of methyl methacrylate with triethylsilane A 200-mL four-necked flask equipped with a Dimroth reflux condenser, stirrer, thermometer and dropping funnel was purged with nitrogen. The flask was charged with 1.9 mg (0.00375 mmol) of tris(pentafluorophenyl)borane, 17.4 g (0.15 mol) of triethylsilane and 581 mg of I-1330, which were stirred at room temperature for 15 minutes. Using an ice bath, the flask was cooled to an internal temperature of 1.5° C. From the dropping funnel, 7.5 g (0.075 mol) of methyl methacrylate was added dropwise over 2.5 hours. During the period of dropwise addition, exothermic reaction took place and the internal temperature rose to 7° C. at maximum. Gas chromatography (GC) analysis confirmed the disappearance of methyl methacrylate after 5 minutes from the completion of dropwise addition. After 2 hours, the ice bath was removed, and the reaction mixture was stirred at room temperature for 18 hours. To the reaction mixture was added 10.5 μL (0.075 mmol) of triethylamine. On GC/MS analysis of the reaction mixture, the main product was the title compound, and none of a carbonyl adduct, a β-adduct as shown below, and derivatives thereof were detected. (Me is methyl, Et is ethyl.)

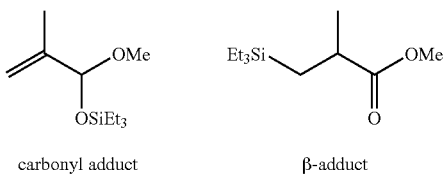

carbonyl adduct          β-adduct

Using a Claisen head having a Vigreux column having an inner diameter of 10 mm and a length of 10 cm, the reaction mixture was distilled in vacuo, whereby 17.9 g of a colorless clear liquid having a boiling point of 108.5–109° C./0.2 kPa was collected. From the results of NMR and GC/MS spectroscopy, the liquid was identified to be the title compound, 1,1-bis(triethylsiloxy)-2-methylpropene. The yield was 75.4% and the purity was >99.9%.

$^1$H-NMR (CDCl$_3$, 300 MHz): δ (ppm) 1.50 (6H, s), 0.98 (18H, t, J=7.9 Hz), 0.67 (12H, q, J=7.9 Hz) $^{13}$C-NMR (CDCl$_3$, 75.6 MHz): δ (ppm) 145.2, 87.1, 17.4, 6.7, 5.1 $^{29}$Si-NMR (CDCl$_3$, 59.7 MHz): δ (ppm) 20.6MS (EI): m/z 316 (M$^+$), 259, 217, 189, 173, 115, 87, 59

Example 7

Synthesis of 1,1-bis(triethylsiloxy)-2-methylpropene through reaction of 1-methoxy-2-methyl-1-triethylsiloxypropene with triethylsilane A 200-mL four-necked flask equipped with a Dimroth reflux condenser, stirrer, thermometer and dropping funnel was purged with nitrogen. The flask was charged with 388 mg of I-1330, 1.28 mg (0.0025 mmol) of tris(pentafluorophenyl)-borane and 5.8 g (0.05 mol) of triethylsilane, which were stirred at room temperature for 15 minutes. Using an ice water bath, the flask was cooled to an internal temperature of 5° C. From the dropping funnel, 10.8 g (0.050 mol) of 1-methoxy-2-methyl-1-triethylsiloxypropene was added dropwise over 3 hours. During the period, the internal temperature rose to 9° C. at maximum. After the completion of dropwise addition, the reaction mixture was stirred at 5° C. for 4 hours and then at room temperature for a further 12 hours. On GC/MS analysis, the formation of the title compound was confirmed. The reaction mixture, to which 9.8 μL (0.07 mmol) of triethylamine was added, was stirred for 0.5 hour and then distilled in vacuo. 11.0 g of a colorless clear fraction having a boiling point of 91–91.50° C./0.13 kPa was collected. From the results of NMR and MS analysis, the liquid was identified to be the title compound, 1,1-bis(triethylsiloxy)-2-methylpropene. The yield was 69.5%.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A process for preparing a disilyl ketene acetal of the general formula (7), comprising the step of reacting a silyl ketene acetal of the general formula (6) with a hydrosilane or hydrosiloxane of the general formula (2) in the presence of a catalytic amount of tris(pentafluorophenyl)borane, wherein $R^9$ and $R^{10}$ are each independently hydrogen or a substituted or unsubstituted monovalent hydrocarbon group of 1 to 60 carbon atoms, or a pair of $R^9$ and $R^{10}$ may bond together to form a ring of 3 to 20 carbon atoms with the carbon atom to which they are attached, $R^{11}$ is a substituted or unsubstituted monovalent hydrocarbon group of 1 to 40 carbon atoms, $R^d$, $R^e$ and $R^f$ are independently selected from a substituted or unsubstituted monovalent hydrocarbon group of 1 to 20 carbon atoms, an organoxy group of 1 to 20 carbon atoms, an organo(poly)siloxy group of 1 to 1,000 silicon atoms, and a halogen atom, or a pair of $R^d$ and $R^e$, $R^d$ and $R^f$, or $R^e$ and $R^f$ may bond together to form a siloxane ring of 3 to 50 silicon atoms or a silicon-containing ring of 1 to 20 carbon atoms with the silicon atom to which they are attached, or $R^d$, $R^e$ and $R^f$ may bond together to form a cage siloxane of 6 to 50 silicon atoms with the silicon atom to which they are attached,

wherein $R^a$, $R^b$ and $R^c$ are independently selected from a substituted or unsubstituted monovalent hydrocarbon group of 1 to 20 carbon atoms, an organoxy group of 1 to 20 carbon atoms, an organo(poly)siloxy group of 1 to 1,000 silicon atoms, and a halogen atom, or a pair of $R^a$ and $R^b$, $R^a$ and $R^c$, or $R^b$ and $R^c$ may bond together to form a siloxane ring of 3 to 50 silicon atoms or a silicon-containing ring of 1 to 20 carbon atoms with the silicon atom to which they are attached, or $R^a$, $R^b$ and $R^c$ may bond together to form a cage siloxane of 6 to 50 silicon atoms with the silicon atom to which they are attached,

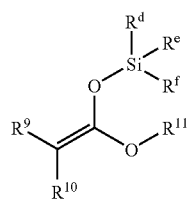

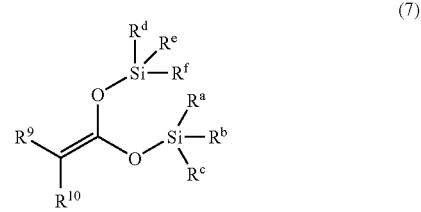

wherein $R^9$, $R^{10}$, $R^a$, $R^b$, $R^c$, $R^d$, $R^e$ and $R^f$ are as defined in formulae (6) and (2).

* * * * *